United States Patent [19]

Inanaga et al.

[11] 4,421,745
[45] Dec. 20, 1983

[54] ANTIEPILEPTICS

[75] Inventors: Kazutoyo Inanaga, Kurume; Yugi Nagawa, Nagaokakyo, both of Japan

[73] Assignee: Takeda Chemical Industries, Ltd., Osaka, Japan

[21] Appl. No.: 416,706

[22] Filed: Sep. 10, 1982

[30] Foreign Application Priority Data

Sep. 16, 1981 [JP] Japan ................................ 56-146946

[51] Int. Cl.³ ............................................ A61K 37/00
[52] U.S. Cl. ................................................. 424/177
[58] Field of Search ............... 424/177; 260/112.5 TR

[56] References Cited

U.S. PATENT DOCUMENTS 4,100,152 7/1978 Fujino et al. ................. 260/112.3 R Primary Examiner—Delbert R. Phillips
Attorney, Agent, or Firm—Wenderoth, Lind & Ponack

[57] ABSTRACT

By using an antiepileptic, which comprises an effective amount of a peptide of the formula:

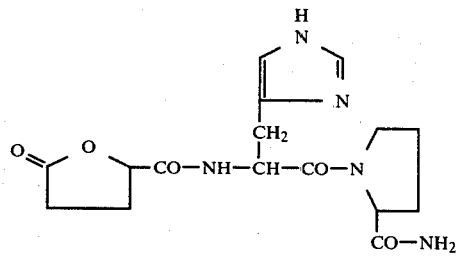

or a physiologically acceptable salt thereof, epilepsy can be improved or cured very effectively without causing side effects.

5 Claims, No Drawings

ANTIEPILEPTICS

This invention relates to antiepileptics and method for treating epileptic patients.

Many of the antiepileptics used clinically hitherto not only inhibit epileptic attacks specifically but also cause a general suppression, though varying in degree, of the central nervous system and these latter properties are also believed to be beneficial to an alleviation or improvement of such episodes. Therefore, such antiepileptics have been commonly administered in severe or refractory epileptic cases for sedating the patients and reducing the incidence of seizures as much as possible through their CNS-suppressant action.

The present inventors found that, unlike these known antiepileptics having CNS-suppressant activity, a certain type of peptide which has central stimulant activity and is thus effective in the improvement of disturbance of consciousness, recovery from anesthesia, treatment of depression, etc., (U.S. Pat. No. 4,100,152) is also very effective in the improvement of mental symptoms, neurological symptoms and electroencephalogram in very intractable cases of epilepsy. This remarkable discovery has resulted in the development of this invention.

Thus, the principal object of this invention is to provide a method for the treatment of an elipetic patient, which comprises administering to said patient an effective amount of a peptide of the formula:

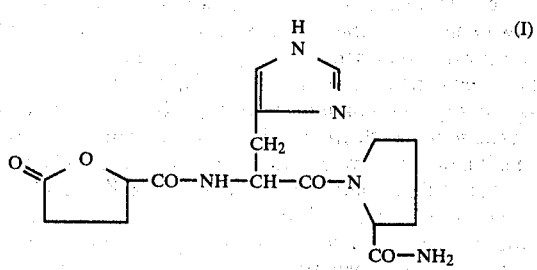

or a physiologically acceptable salt thereof. Another object of this invention is to provide an antiepileptic comprising the aforementioned peptide or its physiologically acceptable salt, which is usable in the aforementioned method.

The antiepileptic according to this invention can be administered to patients in such conditions as major seizures (e.g. diurnal epilepsy, abortive epilepsy, nocturnal epilepsy), minor seizures (e.g. typical absence, atypical absence, astatic seizure, myoclonic seizure, infantile spasm, etc.), psychomotor seizure (e.g. psychic seizure, automatism, etc.), focal seizure (e.g. autonomic seizure, sensory seizure, Jacksonian epilepsy, focal convulsion, adversive seizure, etc.), and so forth. Particularly, the present antiepileptic displays remarkable effects in intractable epilepsy such as myoclonic seizure, Lennox's syndrome, West's syndrome, temporal lobe epilepsy etc.

The amino acid residues forming the peptide of this invention as represented by the formula (I) may be any of the L-, D- and recemic forms, although L-acid residues (γ-butyrolactone-γ-carbonyl-L-histidyl-L-prolinamide) are especially desirable. The γ-butyrolactone-γ-carbonyl residue may be either S- or R-configured.

The above-mentioned peptide may be used as the free peptide or in the form of physiologically acceptable salts thereof, e.g. addition salts such as salts with inorganic acids (e.g. hydrochloride, sulfate, etc.) and organic salts (e.g. acetate, tartrate, citrate, etc.). The citrate is particularly desirable.

The acute toxicity test date on γ-butyrolactone-γ-carbonyl-L-histidyl-L-prolinamide citrate which falls within the scope of said peptide and its physiologically acceptable salts are as follows.

| Route of administration | Acute toxicity ($LD_{50}$, mg/kg) | |
|---|---|---|
| | Mouse | |
| | ♂ | ♀ |
| Intravenous | 558 | 526 |
| Subcutaneous | 3,214 | 4,086 |
| Oral | 13,373 | 13,888 |

(Note)
The compound was administered to ICR strain mice of both sexes by the intravenous, subcutaneous or oral route and each animal so treated was observed for general condition over a period of 7 days.

The dosage of said peptide (I) or salt thereof is selected according to the route of administration, the severity of seizures, etc. By a parenteral route, e.g. i.v. or i.m., generally about 0.1 to 10 mg. of the compound daily is indicated for an adult human. The preferred dose is about 0.5 to 5 mg./adult/day. When the oral, rectal or intranasal route is selected, the dosage is about 1 to 100 mg./adult/day and preferably about 5 to 50 mg./adult/day.

Any pharmaceutical preparation containing said peptide (I) or salt thereof can be produced by the established pharmaceutical procedure and made available in such dosage forms as injectable products, powders, capsules, tablets, pills, etc. For intravenous or intramuscular administration, an injectable solvent such as physiological saline can be employed. For intravenous drip infusion, a diluent such as an aqueous glucose solution can be employed.

If desired, the antiepileptic according to this invention can be used concomitantly with other antiepileptics such as barbiturates (phenobarbital, primidone, etc.), hydantoins (phenytoin, ethotoin, etc), oxazolidines (trimethadione, etc.), succinimides (ethosuximide, etc.), phenacemides (phenacemide, acetylpheneturide, etc.), sulfonamides (sulthiame, acetoazolamide, etc.), aminobutyric acids (e.g. γ-amino-β-hydroxybutyric acid, etc.), adrenocorticotropic hormones (tetracosactide acetate, etc.), benzodiazepines (diazepam, nitrazepam, clonazepam, etc.), sodium valproate, carbamazepine and so on.

With the antiepileptic according to this invention, epilepsy can be improved or cured very effectively without causing side effects.

The following clinical and working examples are further illustrative of this invention. In these clinical, reference and working examples, DN-1417 means (S)-γ-butyrolactone-γ-carbonyl-L-histidyl-L-prolinamide citrate.

CASE 1

Male, 44 years old

With onset of convulsions at age 10, seizures increased in frequency at about age 14, when myoclonus began to appear in his face and extremities, and was especially marked when he, facing another person, was in tension. At age 24, he was seen at another facility, but the myoclonus was refractory. At age 30, he was admitted to another hospital for problematic behavior, such as violet actions against family members, breaking panes of glass and leaving the house at night when excited by trifling incidences. Half a year later, February, 1969 (age 31), he was transferred to our hospital. On admission, he was unable to walk independently, and presented with a lucid consciousness, slow response to questions and slow speech. Jerky, involuntary movements of the face and all extremities were observed. These were exaggerated with photic stimulation or intention movement. Muscular hypotonus, intention tremor and motor incoordination were noted. Tendon reflexes of all extremities were exaggerated, but no pathologic reflexes were noted. With respect to mental status, he displayed poor understanding, a preservation-like tendency, impairment of recent memory and disturbance of judgement. His character was circumstantial, viscous, of childish euphoria and explosive in type. EEG was characterized by multiple spikes and multiple spikes and waves, which were activated with photic stimulation. After admission, he was treated with antiepileptic agents. Convulsions were slightly reduced, but myoclonus was rather aggravated.

After about 3 months of hospitalization, mental symptoms worsened, and were associated with transient appearance of hallucinations and delusions. On a few occasions, because he could not walk independently, he crawled out into the hallway, shouting "Kill me with an injection", or "Give a knife"; on other occasions, he refused foods and drugs, and remained dysphoric. After about 7 months of hospitalization, sodium valproate was prescribed on a trial basis. After about 3 months on this medication, convulsions were inhibited, and he was able to walk, though with difficulty. Frequency of convulsions was reduced to only once a year, but myoclonus remained prominent, exacerbated especially with intention movement or photic stimulation. At meals, he could not manipulate chopsticks but managed to use a spoon.

Dysphoria appeared for approximately 10 days every 2 months, and auditory hallucinations were evident. Typically, he would point at a radiator of a steam heating system or a television set, and shout, "I can hear it from this", or "It is too much. Kill me!". During these periods, myoclonus was aggravated. Because of associated aggravation of ataxia, he was unable to walk independently; consequently, he stayed in bed, covering himself with a coverlet to the head.

He was unable to speak fluently because of dysarthria, and he walked poorly. For these reasons, he came into less and less contact with other patients even when he was in a good mood, preferring to stay in bed or sit on his bed in the ward. Dementia and progressive deterioration of neurological symptoms continued. These clinical manifestations were diagnostic of degenerative myoclonus epilepsy.

In March 1979 (at age 42), the combined administration of clonazepam, 2 mg daily, and other antiepileptics led to the almost complete disappearance of myoclonus at rest, associated with a reduction in myoclonus and tremors on intention, and progressively smoother gait. With prolonged use of clonazepam, it became less effective, but increases in dose have resulted in restoration of the initial effect. No marked progression in neurological manifestations or dementia has been noted since beginning clonazepam in combination with other antiepileptics.

Since about the end of April, 1981, he had been somewhat dysphoric, often staying in bed and showing a tendency to increased twitching. On EEG before DN-1417 administration, slight multiple spikes were noted, associated with activation of polyspike and wave complexes and spike and wave complexes with a 12-f/s flickering light, and also showed intermixing of many electromyographic activities in the basic pattern.

He was given DN-1417, 2 mg. i.m. at 10:00 A.M. every day for 2 weeks concomitantly with the prior antiepileptics.

On the 1st day, he showed no changes in behavior. On the 2nd day, he showed no changes in particular, though he voluntarily walked to bathroom in his usual wide base gait. He became unsteady after 5 or 6 steps, using the wall for support. No other changes were noted.

On the 3rd day, no changes were observed in myoclonus and gait. He was somewhat dysphoric, initially refusing EEG, though he finally complied. No improvement was noted on EEG.

On the 4th day, he was very animated in his facial expressions, which was unprecedented. He also began to watch television in the dayroom after a long hiatus. No changes were noted in sleep, appetite or body temperature.

On the 5th day, he was even more animated, often leaving his ward. During his walks, he seldom used the wall for support, and walked at a somewhat faster pace than usual.

From the 6th day on, he would stay on his ward only for meals and sleeping; otherwise he walked around the hallway and sat in the dayroom watching television and talking with other patients. He participated in all recreation events, moving around actively. He was in a good mood every day, talking frequently, although there was no change in the fluency of his speech. While standing, he maintained the same wide base with feet apart by not less than 10 cm and knees slightly bent. His gait improved in steadiness. Tremors and myoclonus were reduced, and the finger-nose test showed mild dysmetry. He readily participated electroencephalographic examination.

On EEG (at day 8 of DN-1417 treatment), the response to photic stimulation, such as photomyoclonic response, spike and wave complexes, polyspike and wave complexes and polyspikes was entirely normal. The basic pattern changed to a low voltage waves with no intermixing EMG.

So far he had joined walking sessions in the wheel chair but by now would join walking sessions on foot. Though he would be left behind, he declined assistance and walked joyfully over a long distance without falling as if he was confirming his gladness. Thereafter he remained in a good mood throughout the 14-days DN-1417 medication period moving around actively, with myoclonus and motor incoordination reduced.

For 2 days, i.e., on May 19, or the ending day of the 2 week DN-1417 medication, and the following day, he lost his appetite, eating only breakfast, but remained in a good mood, moving actively. Even after withdrawal of the drug, he showed no changes. On EEG 6 days after withdrawal, no photomyoclonic response was noted, although slight intermixing of EMG was seen in the basic pattern.

Beginning from 2 weeks after withdrawal, he left his ward less often, and became less active. On June 8, or about 3 week after withdrawal, he strongly requested to be a pinch hitter in a softball game, and hit grounders to the infield 2 at-bats. However, he could not run.

Later, he walked around the 300 meter playground in about 6 minutes twice, faltering only once. He was dysphoric some days thereafter, making selfish requests, not eating regular meals but much cakes, and staying on his ward. Myoclonus and intention tremor increased slightly, and his gait became more unsteady. About 40 days after withdrawal he seemed to have returned to pretreatment condition. EEG was performed at about 2-week intervals thereafter, but no aggravation was observed without the appearance of the photomyoclonic response. The photomyoclonic response did not reappear until August 7, or about 80 days after withdrawal.

The course of the DN-1417 treatment may be summarized as follows: DN-1417, 2 mg, daily for 2 weeks resulted in improvements in 3 to 4 days; specifically, he became active, began walking without assistance and experienced reduction in myoclonus and tremors. The clinical manifestations improved as a whole without any side effect, continuing for about 1 month after withdrawal of the drug. At day 3, there was no change but at day 8 of treatment, marked improvements in EEG were also seen. The EEGs at 1- to 2-week intervals showed no photomyoclonic response, until about 80 days after the withdrawal when pretreatment patterns returned.

Therefore, DN-1417 was effective in improving myoclonus, cerebellar symptoms, psychic activity and EEG in this case. Its effect on psychic activity was particularly prominent.

Further, because DN-1417 reduced myoclonus and improved cerebellar ataxia, he became less unsteady in his gait, and with increased psychic activity, he was able to walk about the hospital grounds all day. Moreover, clinical improvement appeared at about day 3 of DN-1417 treatment, and persisted for about 1 month after withdrawal of the drug.

Marked EEG improvements appeared on the 2nd EEG taken at day 8 of treatment, and persisted for about 50 days thereafter. From these EEG changes and clinical symptoms, DN-1417 demonstrated an antimyoclonic action though not a definite anticonvulsive action.

CASE 2

Male, 8 years old

Full-term birth, spontaneous labor, asphyxia (-). Birth weight 3630 g., holding the head erect 3 months. In the course of toddling at 10 months, he fell with the head bent forward all of a sudden, whereupon he was examined and diagnosed as epilepsy in the department of pediatrics of A hospital. With the diagnosis of epilepsy, he was placed under an antiepileptic regimen. Though he began to walk at the age of one year and two months, he was hospitalized as a case of Kawasaki disease. Thereafter, the frequency of infantile spasm increased to several to more than 10 times a day. At the age 2 years and 5 months, he was diagnosed as tuberous sclerosis at the department of pediatrics of B hospital and treated there till the age 6 years and 4 months, with a short term of hospitalization during the time. However, seizures with a frequency of 1 to 3 times/day could hardly be controlled. Mental retardation was serious and the speech was as bad as murmurs with poor verbal understanding. Action was slow but restless and unstable. The need for total assistance and medical attention and care was indicated and he was admitted to the S House, an institution for mentally handicapped persons (at 6 years and 6 months). He is now under therapy at a mental clinic T on an outpatient basis. The clinical episode consists mainly of tonic convulsion and atypical absence, although clonic convulsion and myoclonus at extremities are observed at times. As to the incidence of fits, tonic convulsion is seen at the frequency of 2 to 3 times a month, and 3 to 6 seizures of atypical absence are observed on 0 to 2 days a month.

He is now on a multiple drug regimen of 0.18 g. of phenytoin, 0.07 g. of phenobarbital, 20 mg. of nitrazepam and 400 mg. of sodium valproate. The EEG showed a high frequency of polyspike and spikes, associated with occasional appearance of bursts. These are periodic.

CT-scan revealed calcification around the cerebral chamber ventriculus. IQ could not be measured and there was almost no spontaneous speech. Motion was slow but unsettled. Gait was as bad as reeling and unstable. Facial expressions were blurred. Posture was slightly bent forward.

Administration of DN-1417

In conjunction with the antiepileptic drugs so far used, DN-1417 was administered intramuscularly in doses of 0.5 mg. for 10 days and, then, in doses of 1 mg. for 4 days.

Condition after administration of DN-1417

(1) After one week

No clinical episodes. Motion became more agile and gaits were stabilized with less reeling. Facial expressions were less blurred and betrayed smiles on more occasions. Interest in picture books began to be observed.

(2) After 2 weeks

After administration of DN-1417, there had been no clinical episodes. Motion became so quick that he had to be constantly attended. Facial expressions were amicable and clear. The forwardly bent posture became scarcely noticeable. Gait was stable without reeling.

The EEG was basically unchanged, showing diffuse sharp-and-slow wave complexes and polyspike-and-wave complexes but the frequency of paroxymal patterns was halved without evidence of periodicity and bursts which had been observed before the drug administration (Since the EEG at rest could not be measured and only the EEG at sleep could be measured, any comparison should be made only carefully). In this case, high amplitude spindle waves of 150 to 200 $\mu$V for 12 to 14 c/sec. were observed in chains at sleep, there was no particular change in this respect.

(3) One week after withdrawal

On day 4 after withdrawal of the drug, as he forgot to take the drugs during the summer vacation, 4 episodes of tonic convulsion were seen on day 5. Thereafter, compliance was confirmed and there was no episode. However, on the EEG at visit on day 8 after withdrawal, waves which appeared to be "rapid rhythm" of 100 $\mu$V, 10–14 c/sec. persisted generally, bilaterally and synchronously for 3 to 4 seconds, forming bursts. Polyspike-and-slow wave complexes and high voltage slow waves were also observed. However, activities of daily life were brisk and facial expressions were amicable. There was no side effect, whether subjective or objective, nor was there an abnormal finding in any of electrocardiogram, liver function test and routine hematological examination.

This, DN-1417 caused remarkable improvements in daily activity and improvements in clinical episode and EEG. Therefore, the drug was considered to be effective.

CASE 3

Male, 11 years old

Asphyxial birth due to prolonged labor. While once suffered from icterus gravis, he grew substantially normally till the age of about 3 years.

At the age 3 years and 3 months, there was a first episode of infantile spasm, i.e. a forward bending of the neck and a supraduction and fixation of the eyeballs. Many of the seizures came immediately after awakening in early morning and the frequency of seizures was 5 to 10 daily.

At the age 4 years and 10 months, he was examined and treated at the pediatric clinic of a certain university, whereby the frequency of seizures was reduced to 1 to 3 times daily. However, as the seizures could not be controlled well and mental retardation (IQ=42) and hyperkinesia became conspicuous, he was admitted to an institution for mentally handicapped persons at the age 5 years and 6 months. During the short stay in the institution, he visited the outpatient department of this hospital. The clinical seizure type was infantile spasm accompanied by the forward bending of the head and the bending of the extremities, which persisted for a few seconds to more than 10 seconds without forming a series. The EEG showed incessant appearances of hypsarrhythmia and irregular spike-and-slow wave complexes, suggesting a combination of West's syndrome and Lennox's syndrome.

The epileptic episode tended to decrease on account of treatment but was basically unchanged.

At the age of 5 years and 11 months, tonoclonic convulsion appeared and, together with varying degrees of tonic fits, represented a dominant type of seizure. In EEG, diffusely irregular sharp and slow wave complex appeared in clusters or periodically on many occasions. In regard to activities of daily life, hyperkinesia subsided and dull motion came into the foreground.

At 7 years of age, ACTH therapy was given tentatively but with no avail. During the period from 7 years and 3 months to 10 years and 4 months, he was transferred to another hospital for a family affair reason and no detailed course could be established but there was no fundamental change of condition.

At the age 10 years and 4 months, he was reexamined at the outpatient department of this hospital. During the first 2 months after he had reached the age of 10 years and 6 months, he was admitted to our hospital as the frequency of epileptic seizures was so high. After 10 years and 10 months, slow motion, unstable gait and other symptoms became severer and he was readmitted to an institution for mentally handicapped persons and enrolled in a school for physically or mentally handicapped children.

Today, there is a moderate degree of mental retardation and the clinical type of seizures is that of Lennox's syndrome which is mainly characterized by tonic seizure among various secondary diffuse seizures. The maximum frequency is 5 to 6 times/day but tonic seizure occurs at the average rate of once in every 3 days. The anteflexed posture with a head drooped and a back rounded is severe and the gait is wide-base and a very unstable one like drunker's requiring assistant. Drowsiness, a blurred face, a very slow motion and salivation are noted. Voluntary speech is nearly absent and responses are dull and slow.

The treatment consisted of a multiple drug therapy using phenytoin, phenobarbital, sodium valproate, nitrazepam and clonazepam. The blood concentrations were 9.0 $\mu$g/ml of phenytoin, 18.9 $\mu$g/ml of phenobarbital, and 36 $\mu$g/ml of sodium valproate.

The EEG showed frequent and periodic onsets of diffuse sharp-and-slow wave complex and polyspike-and-slow wave complex, with clusters being also observed. The basal wave was irregular and many slow waves of high voltage were observed.

Administration of DN-1417

During the period from July 22 to Aug. 4, 1981, 1 mg of DN-1417 was administered intramuscularly once daily for 14 consecutive days, concomitantly with the antipileptics so far employed.

Condition after medication (1) After one week

There was no clinical episode. The face appeared more amicable and the anteflexed posture corrected to a fair extent, and the activation of motion was observed. Responses considerably got quick but voluntary speech was still seen only occasionally. The gait was stabilized to a fair extent and the wide base narrowed.

The EEG showed a decrease in polyspike-and-slow wave complex but an increase in sharp-and-slow wave complex, particularly that of clusters. The spike-and-slow wave showed an increased slow-wave component as a dominant feature, with an extended period.

(2) After 2 weeks

There was one episode of atypical absence. Absent mindedness was seen on fewer occasions, emotional expression and cheerfulness increased, smiles being observed on more occasions. Sleep during daytime, as well as salivation, decreased. He was seen raising his head and stretching the back, and walked steadily without assistance, though only slowly.

The EEG showed no polyspike-and-slow wave complex and only a decreased sharp-and-slow wave complex. The basal wave consisted mainly of waves 5 to 7 c/sec. but a regularity began to be observed. The blood concentrations of antiepileptics were 18.3 $\mu$g./ml of phenytoin, 24.6 $\mu$g/ml of phenobarbital and 25.1 $\mu$g./ml of sodium valproate. It was worth noting that the blood level of phenytoin was twice as high.

(3) One week after withdrawal

No clinical episode. The improved daily life persisted. The EEG showed less bursts, with an increased regularity of basal wave.

There was no side effect, whether subjective or objective, nor was there a change in any of EEG, liver function and general hematology.

The decreased incidence of clinical episodes, improved EEG findings and remarkable improvements in daily life suggested the effectiveness of DN-1417.

CASE 4

Female, 17 years old

The first daughter, a third child, born without trouble at full term. Birth weight 3500 g. The first son, afflicted by epilepsy and severe mental retardation, had died.

Growth was good during the nursing period. At 2 years and 6 months of age, the fever developed due to measles resulted in a general cramp. Thereafter, heat cramp was noted on 2 occasions.

At 3 years and 6 months, there was a first onset of infantile spasm. She was examined at the pediatric clinic of K university and began to take antiepileptics. Two or 3 seizures occurred daily and could hardly be controlled. At 5 years and 10 months, she was examined at T clinic. On two occasions she was hospitalized but tonic convulsion was seen once to 3 times a month as the antiepileptic medication was adjusted. Up to the fifth grade of the elementary school, she attended regular classes and rode the bicycle, although she was often involved in traffic accidents due to lack of concentration. Atypical absence was not observed.

In April, 1977 (at the age 12 years and 9 months), she was enrolled in the middle school of a school for physically or mentally handicapped children. When she began to lead a dormitory life and onwards, dull motion, persistance and crookedness became noticeable.

In April, 1980 (15 years and 9 months), she entered the high school of the T school for physically or mentally handicapped children but epileptic seizures and the change of character caused difficulties in dormitory life, and was admitted to the S House, an instituting for mentally handicapped persons. (IG=42).

The clinical seizure types were tonic convulsion, tonoclonic convulsion and clonic convulsion, plus myochlonus at the face and extremities. These appeared both in sleep and in waking state but more often at awake. Now, she was placed on a multiple drug regimen consisting of 0.3 g. of phenytoin, 0.05 g. of phenobarbital, 0.5 g. of primidone, 0.5 g. of ethosuximide, 600 mg. of sodium valproate and 4 mg. of nitrazepam. While the frequency of onset was once to twice a month, she had a blurred face with copious salivation and was inactive. Drowsiness was observed. She assumed a sluggish posture most of the time and had a realing, unstable gait. She was fastidious and ready to get crooked and cry for the moon. In dysphoria, she was adamant.

The EEG was mainly composed of $\theta$ waves of 5 to 6 c/sec. and showed sharp-and-slow wave complexes and polyspike-and-slow wave complexes as bursts diffusedly and with a tendency of periodicity.

Administration of DN-1417

During the period from July 22 to Aug. 4, 1981, DN-1417 was administered intramuscularly in daily doses of 1 mg. for 14 days, together with the antiepileptics so far employed.

Condition after medication (1) After one week:

No epileptic seizure. Facial expression became more definitive, the posture solid and the behavior smoother. With a less sleepiness, she slept less hours during the daytime. Responses were quicker, with no apparent dysphoria. The EEG did not show bursts any longer and while the basal wave was predominantly $\theta$ waves of 6 to 7 c/sec., $\alpha$ waves of 8 c/sec. were observed, suggesting a remarkable improvement.

(2) After 2 weeks:

No epileptic seizure. Her posture showed a further improvement and a more vivid facial expression with smiles was seen. No salivation. She did not sleep during the daytime any longer. She was in a good mood and took care of children. She spoke more and showed a crooked attitude by far less often. Though EEG showed a mixed pattern of 8 c/sec $\alpha$ waves and 6 to 7 c/sec $\theta$ waves, there was a fair improvement in continuity, with a regularity. However, as bursts, there were sporadically seen sharp-and-slow wave complexes and polyspike-and-slow wave complexes either diffusedly or in clusters.

(3) Three weeks after withdrawal

Clonic convulsion appeared on day 6 after withdrawal but the activates of daily life remained improved. She was good-tempered, cheerful and cooperative. She responded putting on smiles and acted by far more quickly.

So far, there has been no apparent side effect, whether subjective or objective, nor has been any change in laboratory findings.

The above findings may be summarized as follows.

No change or a slight improvement in clinical seizures.

A moderate improvement in EEG, with a decrease of bursts and an improved basal wave.

A remarkable improvement in activities of daily life and in mental condition.

The overall evaluation is a moderate improvement. Thus, DN-1417 was effective.

CASE 5

Male, 27 years old

Impaired-consciousness seizure occurred at age of 14 (1968) and immediately examined at the department of psychiatry of K university. There, a diagnosis of epilepsy was made. Thereafter, automatism was added and he received therapy as out-patient at the I mental hospital.

After graduation from a university (1977), he found employment but repeatedly lost employment because of frequent occurrences of the seizure. He was hospitalized from 1978 to 1980 at the S epilepsy center to control the seizure. The type of the seizure is so called temporal lobe epilepsy representing a complex partial seizure of the impaired-consciousness seizure and automatism. Sometimes, only automatic seizure was recognized complaining mainly of nausea and headache without accompanying the impaired-consciousness seizure. The frequency of the fits of each of complex partial seizure and autonomic seizure was 1–2 times per week. He had difficulty in getting up in the morning and thought it too much troublesome to do anything.

In addition to the prior medication of antiepileptics (10 tablets of HYDANTOL F® each containing 25 mg. phenytoin, 8 mg. phenobarbital and 17 mg. caffeine and sodium benzoate, 1 g. of carbamazepine, 0.09 g. of phenobarbital and 250 mg. of actazolamide), DN-1417 was intramuscularly administered in dose of 1 mg./day for 2 weeks. During the treatment autonomic seizure occurred once. From the 7th day of the DN-1417 treatment he began to explain his conditions as, "The time to get off the bed from awaking has been shortened." and "Became easy to get to the next action in doing anything." Improvement of such psychic symptoms was maintained for a week after the end of the DN-1417 treatment. Automatism occurred a week after the end of the DN-1417 treatment and impaired-consciousness seizure occurred twice in the 3rd week of post-treatment.

No noteworthy change was recognized in the EEG findings, which represented an irregular pattern of a mixture of the moderate voltage slow $\alpha$ wave and $\theta$ wave as the back-ground activity. A spike focus on the right temporal was recognized as the paroxymal discharge.

Thus, the frequency of the clinical fits was reduced and psychic symptoms such as decrease of volition were improved during the course of the DN-1417 treatment suggesting that DN-1417 was effective in this patient.

CASE 6

Male, 7 months old, West's syndrome

There was asphyxia at birth. A diagnosis of cerebral infantile paralysis was made at the new born period. He was institutionalized to the Y asylum for rehabilitation training at age of 5 months. Mental development retarded and remained at the level of 1-2 months. He has cerebral palsy of the spastic type. Since then, infantile spasm (abruptly bows his head, raises the upper limbs and extends the lower limbs) appeared about 10 times a day forming a series. Arousal EEG showed spikes at the occipital region and sleep EEG showed hypsarhythmia.

Nitrazepam in dosage of 1.5 mg./day was administered in three divided doses to show less frequency of the seizure occurrences (from 10 times a day to 6-7 times a day). Severe drowsiness and stridor appeared so that the rehabilitation training became completely impossible. Therefore, nitrazepam was gradually reduced to 0.6 mg./day. The drowsiness was fairly ameliorated but the frequency of the seizure occurrences was not reduced (10 times a day).

DN-1417 in dosage of 0.03 mg./kg. (0.3 mg./day) was intravenously given for 22 days in addition to the treatment with nitrazepam in dosage of 0.6 mg./day.

After a week, infantile spasm of the duration of 2-3 seconds per time forming a series of 2-3 times occurred more frequently (15-16 times a day), but the drowsiness due to nitrazepam was reduced and he was wide awake and active. EEG remained unchanged. The seizure frequency was reduced to 5-6 times a day from the 2nd week of treatment and remained the same at the 3rd week. He continued to be in vivid conditions from the 1st week to the 3rd week of the DN-1417 treatment.

Two weeks after the end of the DN-1417 treatment, the dosage of nitrazepam was weekly increased to 0.7 mg./day and 0.8 mg./day. His conditions remained the same as those at the end of the treatment. EEG obtained 2 weeks after the DN-1417 treatment did not show hypsarhythmia. The number of polyspikes was reduced and the duration of their appearance was shortened.

No side effects were recognized throughout the whole course. The results suggest that DN-1417 is effective for West's syndrome. In addition, the fact that DN-1417 made the patient very vivid and active suggest that further increase in dosage of antiepileptic drugs becomes feasible to completely suppress the seizure.

REFERENCE EXAMPLE

Production of DN-1417

In 160 ml of acetone was dissolved 8.1 g. of (S)-γ-butyrolactone-γ-carbonyl-L-histidyl-L-prolinamide and the solution was added slowly to a solution of 4.3 g. of anhydrous citric acid in 160 ml of acetone. Precipitates were formed and after the mixture was stirred for a while, the precipitates were collected by filtration and dried in vacuo at 55°-60° C. The product was then lyophilized to give 10 g. of DN-1417 powders. $[\alpha]_D^{20} -20°$ to $-25°$ (c=1.0, $CH_3COOH$).

EXAMPLE 1

A lyophilized product containing 0.5 mg., 1 mg. or 2 mg. of DN-1417 (per vial) is dissolved in 2 ml of sterile physiological saline (containing 5% sorbitol) to give an injectable preparation.

What is claimed is:

1. A method for the treatment of an epileptic patient, which comprises administering to said patient an effective amount of a peptide of the formula:

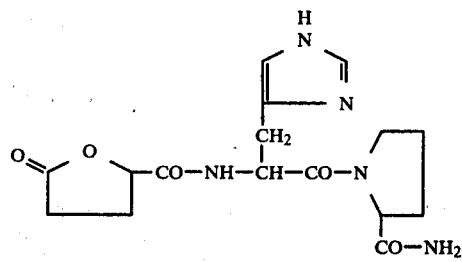

or a physiologically acceptable salt thereof.

2. A method as claimed in claim 1, wherein the peptide is (S)-γ-butyrolactone-γ-carbonyl-L-histidyl-L-prolinamide.

3. A method as claimed in claim 1, wherein the physiologically acceptable salt is the citrate.

4. A method as claimed in claim 1, wherein the peptide or the physiologically acceptable salt thereof is administered parenterally or orally.

5. A method as claimed in claim 4, wherein the peptide or the physiologically acceptable salt thereof is administered intramuscularly in an amount of about 0.1 to 10 mg./adult patient/day.

* * * * *